United States Patent [19]
Belleau et al.

[11] Patent Number: 5,371,185
[45] Date of Patent: *Dec. 6, 1994

[54] 1-AMINO THIORCYL BENZIMIDAZOYL-2-ONE COMPOUNDS

[75] Inventors: Bernard Belleau, late of Quebec, by Pierrette Belleau, executrix; Denis Brillon, Ontario; Gilles Sauve, Quebec; Boulos Zacharie, Quebec, all of Canada

[73] Assignee: Biochem Pharma Inc., Laval, Canada

[*] Notice: The portion of the term of this patent subsequent to Aug. 11, 2009 has been disclaimed.

[21] Appl. No.: 839,609

[22] Filed: Feb. 21, 1992

Related U.S. Application Data

[63] Continuation-in-part of Ser. No. 389,852, Aug. 4, 1989, Pat. No. 5,138,061.

[51] Int. Cl.$^5$ .................. C07K 7/08; C07K 7/06; C07K 5/10; C07K 5/08; C07K 5/06
[52] U.S. Cl. ................... 530/326; 530/327; 530/328; 530/329; 530/330; 530/331; 530/333; 546/199; 548/305.1; 548/306.4; 548/306.1
[58] Field of Search ............. 548/300, 306.4; 546/199; 530/326-331; 540/424

[56] References Cited

U.S. PATENT DOCUMENTS

| | | | |
|---|---|---|---|
| 2,927,116 | 3/1960 | Davoll et al. | 548/306.4 |
| 4,835,166 | 5/1989 | Kitaura et al. | 514/339 |
| 5,138,061 | 8/1992 | Belleau et al. | 546/199 |

FOREIGN PATENT DOCUMENTS 62-255485  11/1987  Japan ................ 548/306.4

*Primary Examiner*—Floyd D. Higel
*Attorney, Agent, or Firm*—James F. Haley, Jr.; Andrew S. Marks; Wendy E. Rieder

[57] ABSTRACT

This invention relates to 1-amino thioacylbenzimidazoyl-2-one derivatives having the formula:

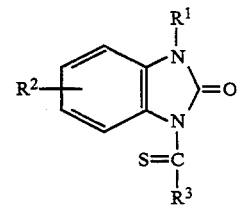

wherein $R^1$, $R^2$ and $R^3$ are defined herein. These compounds are useful as thioacylating reagents. This invention also relates to a process for producing cyclic and linear thiopeptides using the thioacylating reagents of this invention. This invention further relates to intermediate anilide compounds, which are produced by reacting an ortho phenylene diamine with an amino acid chain or peptide. This invention also relates to intermediate thioanilide compounds, which are produced by thionating the intermediate anilide compounds. This invention further relates to a process for producing the thioacylating reagents of this invention by cyclizing the intermediate thioanilide compounds.

6 Claims, No Drawings

1-AMINO THIORCYL BENZIMIDAZOYL-2-ONE COMPOUNDS

This application is a continuation-in-part of U.S. patent application Ser. No. 07/389,852, filed Aug. 4, 1989, now U.S. Pat. No. 5,138,061.

TECHNICAL FIELD OF THE INVENTION

This invention relates to 1-amino thioacylbenzimidazoyl-2-one derivatives and the use of such compounds as thioacylating reagents. This invention also relates to novel intermediates and processes for using them to prepare these thioacylating reagents. The thioacylating reagents of this invention may be used to prepare linear or cyclic thiopeptides. Accordingly, this invention also relates to methods for preparing those thiopeptides and the thiopeptides produced according to these methods.

BACKGROUND OF THE INVENTION

The biological utility of linear and cyclic synthetic peptides is dramatically circumscribed by their short half-lives in vivo and their lack of effectiveness when administered orally. These therapeutic disadvantages are primarily due to the extreme lability of biologically active peptides in the presence of the peptidases and proteases normally found in the digestive tract.

It is, therefore, desirable to stabilize the biologically active peptides against destructive enzymes, such as proteolytic enzymes, in order to improve the pharmacokinetic properties of these peptides. Enhanced stability to enzymatic degradation would also make such peptides more useful as therapeutic agents.

One way to stabilize peptides is to stabilize their backbone amide linkages. Recent advances in chemical replacement and modification of peptide linkages indicate that such linkage stabilization is feasible. In one method, replacement of peptide linkages at positions amenable to peptidase and protease cleavage with thioamide bonds produces analogues that are more stable to enzymatic degradation.

These analogues also display enhanced pharmacological activity. See, for example, G. Lajoie et al., "Synthesis and Biological Activity of Monothionated Analogs of Leucine-enkephalin", *Int. J. Pept. Protein Res.*, 24, p. 316, (1984). Thiopeptide derivatives have also demonstrated increased activity in vivo as biological response modifiers, neuroeffectors, and immunomodulators, as compared with their oxygenated analogs. K. Clausen et. al., "Evidence of a Peptide Backbone Contribution Toward Selective Receptor Recognition for Leucine Enkephalin Thioamide Analogs", *Biochem. Biophys Res Commun.*, 120, p. 305, (1984).

One method for forming a thioamide bond involves replacing the carbonyl oxygen of the native peptide bond with a sulphur, See, for example, K. Clausen et. al., "Studies on Amino Acids and Peptides Part 6. Methods for Introducing Thioamide Bonds into the Peptide Backbone: Synthesis of the Four Monothio Analogues of Leucine Enkephalin", *J. Chem. Soc. Perkin Trans.*, pp. 785-98 (1984) which describes a method of thioacylation using dithioesters to replace the carbonyl oxygen atom with a sulfur atom.

However, the known thioacylation methods suffer from several disadvantages. First, the syntheses of the prior art thioacylating reagents are cumbersome and difficult. Furthermore, these syntheses produce low overall yields of the desired thiopeptide and often produce significant amounts of undesired and difficult to remove by-products. The prior art syntheses are also disadvantageous in that they can only be carried out on a small scale due to difficult purification schemes and extremely toxic reagents.

Further, the optical integrity of thiopeptides produced by these prior art methods is often not maintained. This further reduces the potential use of the thiopeptides as pharmacological agents.

Finally, the prior art thioacylation methods are limited to the production of linear thiopeptides. They deliver a single thionated amino acid to the N-terminus a growing linear peptide chain. Accordingly, these methods cannot be used to improve the stability and biological activity of known cyclic peptides by replacing peptide bonds in them with thioamide bonds.

For the reasons recited above, there is a need for a thioacylating reagent which is capable of catalyzing the formation of both linear and cyclic thiopeptides. In addition, there is a need for a thioacylating process which can be run on a large scale while producing thiopeptides in high overall purity and yield. There is also a need for a thioacylating process which will retain the optical integrity of the product thiopeptides. There is also a need for cyclic thiopeptides which demonstrate superior biologically useful characteristics, such as increased resistance to enzymatic degradation and improved pharmacological activity.

SUMMARY OF THE INVENTION

It is a principle object of this invention to provide thioacylating reagents, intermediates useful in preparing those reagents and thiopeptides produced using those reagents which solve the above-mentioned problems.

The thioacylating reagents of this invention are 1-amino thioacylbenzimidazoyl-2-one derivatives having the formula:

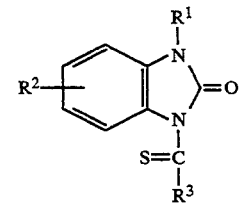

wherein $R^1$ is selected from the group consisting of hydrogen and $C_1$–$C_4$ branched or unbranched alkyl;

$R^2$ is selected from the group consisting of hydrogen, halo, amino, hydroxy, $C_1$–$C_4$ branched. or unbranched alkoxy, aryl, amido, acyl, carboxy, cyano, mercapto, nitro, azido, and $C_1$–$C_4$ branched or unbranched alkyl optionally substituted by halo, amino, hydroxy, $C_1$–$C_4$ branched or unbranched alkoxy, guanido, amido, acyl, carboxy, cyano, mercapto, nitro, or azido; and $R^3$ is an amino acid chain consisting of at least two amino acid residues.

It is also an object of this invention to provide processes for producing linear and cyclic thiopeptides using the thioacylating reagents of this invention.

It is also an object of this invention to provide linear and cyclic thiopeptides produced by the processes of this invention.

DETAILED DESCRIPTION OF THE INVENTION

In accordance with this invention, the following definitions apply:

amino acid or amino acid residue—a chemical moiety having an N-terminus and a C-terminus (being either a C=O or C=S terminus) separated by a single carbon atom As used herein, 'amino acid' refers either to the free, unbound form, the form bound by either a peptide or a thiopeptide bond at a single terminus (either the N-terminus or the C-terminus) or the form bound at both the N- and the C-termini via peptide or thiopeptide bonds. This term encompasses all of the naturally occurring amino acids, those amino acids in their D-configurations, and non-native, synthetic and modified amino acids such as homocysteine, homoserine, diaminobutyric acid, ornithine, norleucine and 2-amino-5-hydroxy pentanoic acid. The term 'amino acid' also includes those carrying side chains which are protected with any protecting group, as well as the unprotected or deprotected, free form.

peptide—two or more amino acid residues covalently bound via a peptide bond. A peptide is also called an amino acid chain.

thiopeptide—two or more amino acid residues covalently bound via peptide bonds, at least one of which is a thiopeptide bond.

cyclic thiopeptide—refers to a peptide containing a ring, the ring being characterized by a >+C=S member. A cyclic thiopeptide formed by covalently binding the N-terminus of a thiopeptide intramolecularly to its C-terminus through the >+=S moiety is called a "terminus-to-terminus cyclic thiopeptide". A cyclic thiopeptide formed by covalently binding a side chain bound to a thiopeptide intramolecularly to the >+C=S moiety is called a "side chain cyclized thiopeptide".

halo—a chemical moiety selected from the group consisting of fluoro, chloro, bromo and iodo.

The thioacylating reagents of this invention are typically prepared by the following reaction scheme:

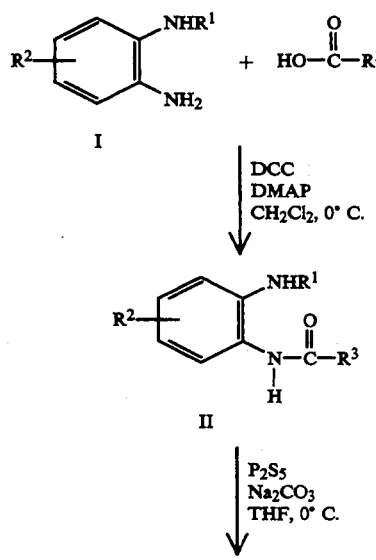

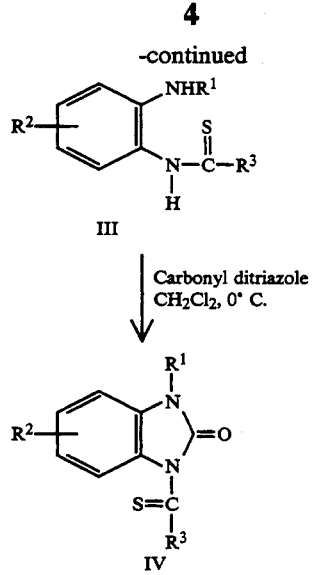

wherein $R^1$ is selected from the group consisting of hydrogen and $C_1$-$C_4$ branched or unbranched alkyl;

$R^2$ is selected from the group consisting of hydrogen, halo, amino, hydroxy, $C_1$-$C_4$ branched or unbranched alkoxy, aryl, amido, acyl, carboxy, cyano, mercapto, nitro, azido, and $C_1$-$C_4$ branched or unbranched alkyl optionally substituted by halo, amino, hydroxy, $C_1$-$C_4$ branched or unbranched alkoxy, guanido, amido, acyl, carboxy, cyano, mercapto, nitro, or azido; and $R^3$ is the residue of $R^3COOH$, an amino acid chain or peptide consisting of at least two amino acid residues.

As the above scheme demonstrates, an ortho-phenylene diamine (I) and $R^3COOH$ may be reacted in the presence of a peptide coupling agent to form an amino acid ortho amino anilide (II). Surprisingly, however, in this reaction, selective amide formation occurs at only one of the two amino substituents on the benzene ring. Contacting II with a thionation reagent forms an amino acid ortho amino thioanilide (III). Subsequent treatment of III with an amino reactive reagent yields the desired thioacylating reagent (IV).

Coupling of an ortho-phenylene diamine (I) with $R^3COOH$, as described above, may be accomplished by employing established techniques in the field of peptide chemistry. A broad range of suitable reactions are described in E. Gross & J. Meinhofer, *The Peptides: Analysis, Synthesis, Biology: Modern Techniques of Peptide and Amino Acid Analysis*, (John Wiley & Sons, 1981) and M. Bodanszky, *Principles Of Peptide Synthesis*, (Springer-Verlag, 1984). The peptide coupling agents which may, for example, be used to include N,N'-dicyclohexylcarbodiimide (DCC), N,N'-carbonyl diimidazole (CDI), 1-hydroxy benzotriazole (HOBt) and ethyl chloroformate. The preferred coupling reagent is DCC. DCC may be used with or without catalytic additives such as 4-dimethylaminopyridine (DMAP), copper (II) chloride or HOBt. Such catalysts may increase the rate of reaction while suppressing the racemization of the desired compound. The use of DCC together with DMAP is most preferred.

The preferred, DCC, DMAP catalyzed reaction is typically performed in a solvent that is inert with respect to the reactants. The solvent is normally an organic solvent which is polar and aprotic. Preferred solvents include dichloromethane, chloroform, diethyl ether, tetrahydrofuran (THF) and N,N'-dimethylformamide (DMF). Particularly preferred solvents are dichloromethane and DMF. The coupling reaction is run under atmospheric pressure at a temperature of −78° C. to reflux for a period of about 1–48 hours. Preferably, the reaction is carried out at −10° C. to 25° C. with stirring, shaking or agitation over a period of 4–6 hours.

Compounds of formula III are typically prepared under anhydrous conditions, by reacting compounds of formula II with a mixture of phosphorous pentasulfide and anhydrous sodium carbonate in an inert solvent. The solvent is preferably anhydrous THF but other suitable solvents include dichloromethane, diethyl ether and DMF. The reaction temperature is preferably about 0° C. but may be varied from −78° C. to gentle reflux.

Compounds of formula IV may be prepared by contacting a compound of formula III with an amino reactive compound suited for internal ring closure, such as carbonyl ditriazole or a mixture of triphosgene/2,4,6-collidine in an inert solvent at a temperature of −78° C. to gentle reflux, preferably room temperature. The solvent may be selected from, but is not limited to, dichloromethane, diethyl ether, DMF and THF.

As will be appreciated by one of skill in the art, residue $R^3$ of peptide R3COOH must be protected during the above-described reactions. The protecting groups are then removed at appropriate points in the reaction scheme, i.e., to allow cyclization or coupling of the peptide. As known in the art the protecting groups should be capable of introduction to $R^3$ efficaciously and their removal should be performed under conditions which do not adversely affect other portions of the molecule. In this manner, certain reactions and modifications may be performed with assurance that the protected functionality will not interfere with the desired reaction. Further, by choosing a protecting group that is sensitive and labile to certain reactive conditions, a reaction scheme may be outlined to easily and efficiently remove the protecting group once the synthesis is complete.

A variety of protecting groups known in the field of peptide synthesis for reactive functional groups may be found in T. Greene, *Protective Groups In Organic Synthesis*, (John Wiley & Sons, 1981). The appropriate protecting group to use in a particular synthetic scheme will depend on many factors, including the presence of other reactive functional groups and the reaction conditions desired for removal.

In any of the synthetic methods described above, the desired products may be isolated from the reaction mixture by crystallization. Alternatively, other techniques may be used alone, or in addition to crystallization. Such additional techniques include chromatographic separations (for example, normal phase, reverse-phase, ion-exchange, affinity and gel permeation), as well as electrophoresis, extraction and other known means.

The thioacylating reagents of this invention are 1-amino thioacylbenzimidazoyl-2-one derivatives of the formula:

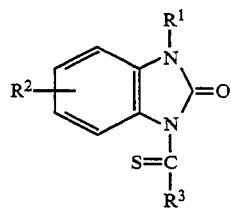

wherein $R^1$, $R^2$ and $R^3$ are defined above.

$R^1$ is typically hydrogen, although any lower alkyl ($C_1$–$C_4$) group which does not interfere with the synthesis of the thioacylating reagents is preferred. When $R^1$ is an alkyl group, overall retention of optical purity is improved because of stearic considerations.

$R^2$ is hydrogen or preferably an electron withdrawing substituent. The preferred electron withdrawing substituents include amido, halo, aryl, acyl, carboxy, cyano, nitro and azido. Use of an electron withdrawing substituent adjusts the degree of activation afforded to the thiocarbonyl carbon. By altering this activation level, difficult cyclization reactions may be driven towards completion, without sacrificing reaction-site specificity or forming undesired polymerization by-products.

$R^3$ is the residue of $R^3COOH$, an amino acid chain or polypeptide consisting of at least two amino acid residues. Preferably $R^3COOH$ contains naturally occurring amino acids. For the sake of clarity, as referred to herein, the position of each amino acid residue $R^3COOH$ may be referred to by a number, in ascending order, position 1 being the residue attached directly to the COOH moiety.

In one embodiment of this invention,—the use of compound IV as a thioacylating reagent—$R^3$—C═S may be transferred from thioacylating agent (IV) to a growing peptide chain. The product is, thus, a linear thiopeptide in which the thioamide bond is selectively located by choosing when the thioacylating reagent is added to the reaction mixture.

The thioacylating reaction is carried out in a suitable inert solvent in the presence of an appropriate peptide coupling reagent. The preferred inert solvents include dichloromethane, chloroform, diethyl ether, THF and DMF. Particularly preferred solvents are dichloromethane and DMF. Typically, reaction conditions are from −78° C. to gentle reflux for a period of about 1–48 hours. Particularly preferred conditions are −10° C. to 25° C. for a period of 4–6 hours.

Until the $R^3$—C═S linkage is required to be introduced into the polypeptide chain, the peptide may be synthesized under any peptide coupling conditions. Alternatively, the thioacylating reagent may be introduced first and the thiopeptide so formed may then be enlarged employing generally recognized peptide coupling conditions. However, it is most advantageous to first synthesize $R^3COOH$ so as to include all amino acid residues derived in the ultimate thiopeptide following the thioamide linkage. In this embodiment, addition of the thioacylating reagent to a solution of the growing peptide completes the desired thiopeptide. Because formation of the thioamide linkage requires only a single coupling step, optical purity of the final peptide is most easily monitored and maintained in this manner. In addition, overall yields and reaction-site specificity are improved. Also, product characterization is facilitated because the final thiopeptide may be formed from two well characterized fragments.

Once the product thiopeptide is formed, it may be freed of its protecting groups according to well-known protocols such as treatment with liquid hydrogen fluoride (HF). Where, however, selective removal of the protective groups, such as from the amino terminus only, is desired suitable reaction conditions must be employed. Those conditions are also well known in the art.

An alternative synthetic approach for introducing thioamide linkages to peptides using the thioacylating reagents of this invention is Merrifield solid phase synthesis and its known variants. Thus, a Merrifield resin is prepared by well-known solid phase peptide synthetic methods. A covalently attached α-amino acid residue, attached at its C terminus or, similarly, a peptide with a free terminal amino functionality is carried by the resin. Treatment of the resin with a thioacylating reagent according to this invention under standard conditions will afford the desired product in a single step, if, as is preferred, the $R^3$ residue includes all of the desired amino acids downstream of the thioamide band. Alternatively, elongation of the thiopeptide chain may continue after the thioamide linkage is formed. Thioamide linkages using the thioacylating reagents of this invention can also be introduced into peptides in automated peptide synthesizers using established synthetic techniques.

The completed thiopeptide may be liberated from the resin by using well-established methods. After freeing the thiopeptide from the resin, it may be deprotected as above.

In an alternative and preferred embodiment of this invention, the thioacylating reagents may be used to form cyclized thiopeptides. For example, a deprotected, N-terminus of $R^3$ in IV may cyclize intramolecularly with the thiocarbonyl moiety to form a terminus-to-terminus cyclic thiopeptide. As described above, selective deprotection of the amino terminus is easily accomplished by know techniques.

Alternatively, a side chain on $R^3$ in IV having a deprotected nucleophilic moiety (such as an amino group, a sulfhydryl group or a hydroxy group) may cyclize intramolecularly with the thiocarbonyl to form a side chain cyclic thiopeptide. In this case, the cyclic portion of the thiopeptide is limited to the c-terminal region. The portion of the $R^3$ amino acid chain not involved in the cycle extends out from the cycle, ending with the N-terminus.

In either the terminus-to-terminus or side chain cyclized thiopeptide, the efficacy of ring formation is dependent upon several factors. First, certain rings are known to be more energetically favorable than others. For instance, 4-, 5- and 6-membered rings form more easily than 3-membered rings and are more stable. The favored ring sizes are those rings with 4-, 5-, 6-, 7-, 12-, 15- and 18-members. Therefore, in the case of terminus-to-terminus cyclic thiopeptides, $R^3$ is preferably 2–15 amino acids and more preferably 2–10 amino acids. Within this range, the most favorable ring structures will form.

Preferred $R^3$ groups for terminus to terminus cyclization include biologically active amino acid chains that cyclize spontaneously in their free peptide form. Examples of such preferred $R^3$ amino acid chains include:

(a) Pro-Phe-D-Trp-Lys-Thr-Phe;
(b) Thz-Phe-D-Trp-Lys-Thr-Phe;
(c) Thz-Phe-D-Trp-Lys-Thr-gPheC=O;
(c) gSar-R,S-mPhe-D-Trp-Lys-Thr-Phe;
(d) Pro-Phe-D-Trp-Lys-gVal-R,S-mPhe;
(e) Arg-Lys-Asp-Val-Tyr; and
(f) Arg-Lys-Asp-Val-Tyr-Gly.

wherein Thz represents thioproline, g represents an inverted amino acid, m represents an N-methylated amino acid and R,S represents a mixture of R and S isomers.

The structures and biological activity of these cyclic peptides are discussed in C. Pattaroni et al., "Cyclic Hexapeptides Related to Somatostatin", *Int. J. Peptide Protein Res.*, 36, pp. 401–17 (1990) ((a)–(d)) and G. A. Heavner et al., "Biologically Active Conformations of Thymopentin", *Int. J. Peptide Protein Res.*, 37, pp. 198–209 (1991) ((e) and (f)). It is be expected that the thionated analogs of these cyclic peptides would demonstrate longer in vivo half lives and greater biological activity than their oxygenated counterparts.

In the case of side chain cyclized thiopeptides, the preferred side chains are also those that tend to form rings of favorable sizes. These side chains include, but are not limited to, those carried by the following amino acids, when they are located in position 1 of $R^3$: diaminobutyric acid, homoserine, homocysteine, ornithine 2-amino-5-hydroxy pentanoic acid. Cysteine and serine in position 2 also result in favorable side claims for side chain cyclization in accordance with this invention.

In order that this invention be more fully understood, the following examples are set forth. These examples are for the purpose of illustration only, and are not to be construed as limiting the scope of the invention in any way.

In each example, reaction concentrations are generally held at 0.1 M of the reactants, but a higher or lower concentration may be used in cases where the specific reaction is favorably influenced. In practice, the amounts of reagents will change depending upon variations in reaction conditions and the nature of the reactants themselves.

EXAMPLE 1

Preparation of
α-N-Boc-L-alanyl-L-valyl-L-alanyl-L-tyrosinyl-O-benzyl-benzyl ester-3-thioamide I. Synthesis of
1-(α-N-Boc-L-alanyl-L-valyl-thioacyl)-2-benzimidazolone a) Preparation of α-N-Boc-L-alanyl-L-valyl-ortho amino anilide α-N-Boc-L-alanyl-L-valyl benzyl ester (about 8 mmol) and ortho-phenylene diamine (about 11 mmol) are well dissolved in dichloromethane (20 ml) at 0° C. and N,N'-dicyclohexylcarbodiimide (DCC) (8 mmol) is added. The mixture is stirred for 1 hour at constant ice temperature and then filtered. The filtrate is transferred to a separating funnel and washed successively with saturated brine, 5% aqueous citric acid and 5% aqueous sodium bicarbonate, followed by saturated brine alone. The organic phase is then dried, concentrated, and the residue purified by flash chromatography on silica gel employing a 3:1 hexane-ethyl acetate solvent as an eluant to yield the α-N-Boc-L-alanyl-L-valyl-ortho amino anilide as a solid. The product is recrystallized to analytical purity with a dichloromethane/pentane mixture or alternatively, purified by flash chromatography on a silica gel column, using 1:1 hexane/ethyl acetate as the elutant.

b) Synthesis of α-N-Boc-L-alanyl-L-valyl-ortho amino thioanilide

Phosphorous pentasulfide (6.25 mmol) is added to freshly distilled tetrahydrofuran (THF) (70 ml) followed by anhydrous sodium carbonate (6.25 mmol). The mixture is stirred at 20° C. for 0.3 hours. The mixture is then cooled to 0° C., followed by the addition of the N-Boc-L-alanyl-L-valyl-ortho-amino anilide of step (a) (0.7 mmol). After standing at 0° C. for 5–6 hours, 10% aqueous sodium phosphate (tribasic; 20 ml) is added slowly followed by ethyl acetate (20 ml) and hexane (10 ml). The organic phase is separated, washed with brine, dried, and concentrated. The product oil may be purified by flash chromatography on silica gel using a 3:2 hexane/ethyl acetate eluant to give the α-N-Boc-L-alanyl-L-valyl-ortho amino thioanilide as a crystalline solid.

c) Synthesis of 1-(α-N-Boc-L-alanyl-L-valyl-thioacyl)-2-benzimidazalone

The α-N-Boc-L-alanyl-L-valyl-ortho amino thioanilide of step (b) (3 mmol) and carbonyl ditriazole (4 mmol) are dissolved in THF (45 ml) and after stirred at 25° C. for 6.5 hours. The solvent is then removed in vacuo. The remaining residue is dissolved in dichloromethane (2 ml) and purified by flash chromatography, eluting with 1:1 hexane/ethyl acetate to give pure 1-(α-N-Boc-L-alanyl-L-valyl-2-thioacyl)-2-benzimidazolone.

II. Coupling α-N-Boc-L-alanyl-L-tyrosinyl-O-benzyl ether benzyl ester with 1-(e-N-Boc-L-alanyl-L-valyl-thioacyl)-2-benzimidazolone a) Solution phase α-N-Boc-L-alanyl-L-tyrosinyl-O-benzyl ether benzyl ester is treated with trifluoroacetic acid (TFA) at 0° C. under a flow of nitrogen for 0.5 hours. The TFA is removed in vacuo to yield the L-alanyl-L-tyrosinyl-O-benzyl ether benzyl ester TFA salt. The TFA salt is then dissolved in methylene chloride and treated with 5% aqueous sodium bicarbonate. The organic phase is separated, dried and concentrated to give the free dipeptide derivative.

The resulting free peptide derivative (2 mmol) is dissolved in anhydrous N,N'-dimethylformamide (DMF, 0.5 ml) at 0° C. under nitrogen and 1-(α-N-Boc-L-alanyl-L-valyl-2-thioacyl)-2-benzimidazolone (2.2 mmol) is added in portions at 0° C. with stirring over a 0.3 hour period. The mixture is stirred continuously at 0° C. for 2 hours and allowed to warm to 25° C. overnight. The reaction is then filtered and concentrated in vacuo. The residue is dissolved in ethyl acetate (15 ml) and the solution washed successively with 5% aqueous sodium bicarbonate, water, 5% aqueous citric acid and brine. The organic phase is then dried, followed by evaporation and the residue is placed on a flash column of silica gel for purification using 1:1 hexane/ethyl acetate as the elutant.

b) Solid phase

α-N-Boc-L-alanyl-L-tyrosinyl-O-benzyl ether attached to a benzyloxy group of a Merrifield resin is treated with 55% dichloromethane solution of TFA at room temperature for 1 hour. The resin is then collected, washed successively with four portions of 10 ml dichloromethane, four portions of 10 ml isopropanol (IPA) and dried for subsequent use.

L-alanyl-L-tyrosinyl-O-benzyl ether attached to a benzyloxy group of a Merrifield resin (0.6 mmol/g of resin) is added to a solution of 1-(e-N-Boc-L-alanyl-L-valyl-2-thioacyl)-2-benzimidazolone (1 mmol) in dry DMF (7 ml) with stirring at 25° C. The reaction is stirred for 16 hours after which time another portion of the benzimidazolone (1 mmol) is added and stirring resumed for 18 hours. The α-N-Boc-L-alanyl-L-valyl-L-alanyl-L-tyrosinyl-O-benzyl ether-3-thioamide-resin ester is collected, washed with four 10 ml portions of DMF, then four 10 ml portions of IPA and subsequently dried in preparation for further reaction.

α-N-Boc-L-alanyl-L-valyl-L-alanyl-L-tyrosinyl-0-benzyl ether-3-thioamide-resin ester (0.5 mmol) is treated with liquid hydrogen fluoride (5 ml) containing anisole, dimethyl sulfide, and thioanisole (0.5 ml 1:1:1 v/v) at 0° C. for 1 hour. After evaporation of the solvent, the residue is dissolved in 10% aqueous acetic acid. The aqueous solution is washed with diethyl ether (30 ml), eluted with water and lyophilized to dryness. The crude product is dissolved in 92% aqueous acetic acid (25 ml) and purified by reverse phase chromatography employing a $C_{18}$ packed column and the same acetic acid solvent as the eluant to give α-N-Boc-L-alanyl-L-valyl-L-alanyl-L-tyrosinyl-0-benzyl ether-3-thioamide.

EXAMPLE 2

Preparation of a Terminus-to-Terminus Cyclic Thiopeptide: Cyclic 1-thio-L-alanyl-L-alanine 1-(α-N-Boc-L-alanyl-L-alanyl-thioacyl)-2benzimidazolone, prepared according to the procedure described in Example 1, is treated with trifluoroacetic acid (TFA) at 0° C. under nitrogen for 1 hour. The TFA is removed in vacuo to yield the TFA salt of the dipeptide. The TFA salt is dissolved in dichloromethane and treated with 5% aqueous sodium bicarbonate. The organic phase is separated, dried and concentrated. DMF is added and the reaction is stirred overnight. The solution is then evaporated under reduced pressure and the residue is purified by silica gel flash chromatography, using 1:1 hexane/ethyl acetate as the elutant, to yield the terminus-to-terminus cyclic thiopeptide, cyclic 1-thio-L-alanyl-L-alanine.

EXAMPLE 3

Preparation of a

Side Chain Cyclized Thiopeptide:
Cyclic β-Cysteinyl-S-2-thioalanine 1-(α-N-Boc-L-cysteinyl-S-tert-butyl-L-alanyl-thioacyl)-2-benzimidazolone, prepared according to the procedure described in Example 1, is treated with TFA at 0° C. under argon for 2 hours. The TFA is evaporated under high vacuum to yield the corresponding TFA salt. The TFA salt is dissolved in dichloromethane and treated with 5% aqueous sodium bicarbonate. The organic phase is separated, dried and concentrated. DMF is added and the reaction is stirred for 18 hours. The solution is then evaporated under reduced pressure and the solid is purified by flash chromatography, using 1:1 hexane/ethyl acetate as the elutant, to yield the desired side chain cyclized thiopeptide, cyclic β-cysteinyl-S-2-thioalanine.

What is claimed is:

1. A thioacylating reagent of the formula:

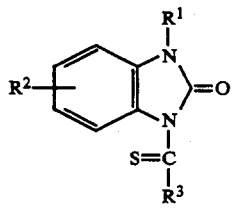

wherein R¹ is selected from the group consisting of hydrogen and $C_1$–$C_4$ branched or unbranched alkyl;

R² is selected from the group consisting of hydrogen, halo, amino, hydroxy, $C_1$–$C_4$ branched or unbranched alkoxy, aryl, amido, acyl, carboxy, cyano, mercapto, nitro, aziode, and $C_1$–$C_4$ branched or unbranched alkyl, unsubstituted or substituted by halo, amino, hydroxy, $C_1$–$C_4$ branched or unbranched alkoxy, guanido, amido, acyl, carbody, cyano, mercapto, nitro, or azido; and R³ is a decarboxylated peptide consisting of at least two amino acid residues.

2. The thioacylating reagent according to claim 1, wherein R³ consists of between 2 and 15 amino acid residues.

3. The thioacylating reagent according to claim 2, wherein R³ consists of between 2 and 10 amino acid residues.

4. The thioacylating reagent according to any one of claims 1, 2 or 3, wherein R³ contains a homocysteine, homoserine, diaminobutyric acid, ornithine or 2-amino-5-hydroxy pentanois acid residue in position 1

5. The thioacylating reagent according to any one of claims 1, 2 or 3, wherein R³ contains a cysteine or serine residue in position 2.

6. The thioacylating reagent according to any one of claims 1, 2 or 3, wherein R³ is selected from the group consisting of:
(a) Pro-Phe-D-Trp-Lys-Thr-Phe;
(b) Thz-Phe-D-Trp-Lys-Thr-Phe;
(c) Thz-Phe-D-Trp-Lys-Thr-gPheC=O;
(d) gSar-R, S-mPhe-D-Trp-Lys-Thr-Phe;
(e) Arg-Lys-Asp-Val-Tyr; and
(f) Arg-Lys-Asp-Val-Tyr-Gly.

* * * * *